United States Patent [19]
Yates et al.

[11] Patent Number: 5,709,680
[45] Date of Patent: *Jan. 20, 1998

[54] ELECTROSURGICAL HEMOSTATIC DEVICE

[75] Inventors: David C. Yates, West Chester; Jesse J. Kuhns, Cincinnati; Warren P. Williamson, IV, Loveland, all of Ohio

[73] Assignee: Ethicon Endo-Surgery, Inc., Cincinnati, Ohio

[*] Notice: The term of this patent shall not extend beyond the expiration date of Pat. No. 5,403,312.

[21] Appl. No.: 362,065

[22] Filed: Dec. 22, 1994

Related U.S. Application Data

[63] Continuation-in-part of Ser. No. 95,797, Jul. 22, 1993, Pat. No. 5,403,312, and Ser. No. 96,154, Jul. 22, 1993, abandoned.

[51] Int. Cl.$^6$ .................................................. A61B 17/36
[52] U.S. Cl. ............................ 606/50; 606/41; 606/45; 606/46; 606/51
[58] Field of Search .................... 606/41, 42, 45, 606/52, 205, 209, 142, 143

[56] References Cited

U.S. PATENT DOCUMENTS

| | | |
|---|---|---|
| 2,031,682 | 2/1936 | Wappler et al. . |
| 4,608,981 | 9/1986 | Rothfuss et al. . |
| 4,633,874 | 1/1987 | Chow et al. . |
| 4,655,216 | 4/1987 | Tischer . |
| 4,671,274 | 6/1987 | Sorochenko . |
| 4,985,030 | 1/1991 | Melzer et al. .................... 606/51 |
| 5,057,107 | 10/1991 | Parins et al. ..................... 606/48 |
| 5,085,659 | 2/1992 | Rydell ............................... 606/47 |
| 5,098,431 | 3/1992 | Rydell ............................... 606/48 |
| 5,104,025 | 4/1992 | Main et al. . |
| 5,151,102 | 9/1992 | Kamiyama et al. .............. 606/52 |
| 5,171,255 | 12/1992 | Rydell ............................. 606/170 |
| 5,190,541 | 3/1993 | Abele et al. ..................... 606/46 |
| 5,201,900 | 4/1993 | Nardella ......................... 606/157 |
| 5,207,691 | 5/1993 | Nardella ......................... 606/142 |
| 5,217,458 | 6/1993 | Parins ............................... 606/48 |
| 5,290,286 | 3/1994 | Parins ............................... 606/50 |
| 5,342,381 | 8/1994 | Tidemand ....................... 606/174 |
| 5,352,222 | 10/1994 | Rydell ............................... 606/52 |
| 5,360,428 | 11/1994 | Hutchinson, Jr. ................. 606/45 |
| 5,389,098 | 2/1995 | Tsuruta et al. .................... 606/41 |
| 5,403,312 | 4/1995 | Yates et al. ....................... 606/49 |
| 5,417,687 | 5/1995 | Nardella et al. .................. 606/32 |
| 5,443,463 | 8/1995 | Stern et al. ....................... 606/51 |
| 5,458,598 | 10/1995 | Feinberg et al. ................. 606/52 |

FOREIGN PATENT DOCUMENTS

| | | |
|---|---|---|
| 0 517 244 | 12/1992 | European Pat. Off. . |
| 0 518 230 | 12/1992 | European Pat. Off. . |
| 0517244A1 | 12/1992 | European Pat. Off. . |
| 0624348A3 | 11/1994 | European Pat. Off. . |
| 0640317A1 | 3/1995 | European Pat. Off. . |
| 4032471A1 | 4/1992 | Germany . |
| WO93/08754 | 5/1993 | WIPO . |
| WO94/24949 | 11/1994 | WIPO . |
| WO94/24951 | 11/1994 | WIPO . |

OTHER PUBLICATIONS

European Search Report Communication dated Jun. 25, 1996.
Automatically Controlled Bipolar Electrocoagulation—"COA–COMP", Neurosurg. Ref. (1984) 187–190; B. Vallofors and B. Bergdahl.
Instrument for Stomach Resection and Bowel Anastomosis Used During Closed Procedures, Department of Surgery of Mukachevo City Hospital, N.G. Vittenberger, Jan.–Feb. 1958, First issue (the 211th).

*Primary Examiner*—Jennifer Bahr
*Assistant Examiner*—Michael Peffley

[57] ABSTRACT

An electrosurgical instrument is provided for cauterization and/or welding of tissue of varying impedances, thicknesses and vascularity especially in the performance of endoscopic procedures. The instrument compresses the tissue in the compression zone between first interfacing surface and second interfacing surfaces. The compression zone is formed by an insulator which forms a compression ridge in one of the interfacing surfaces and separates first and second electrically opposite electrodes. A preferred application of the invention is in a cutting instrument wherein a hemostatic line is formed using RF along a cut line.

17 Claims, 8 Drawing Sheets

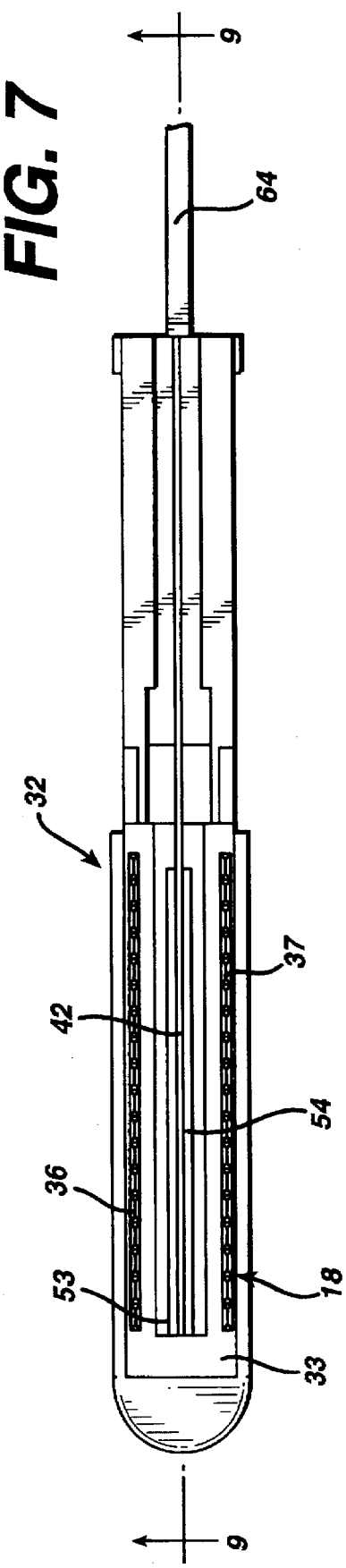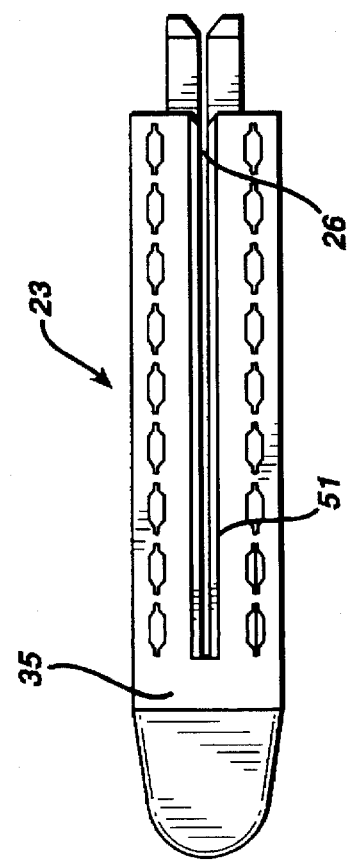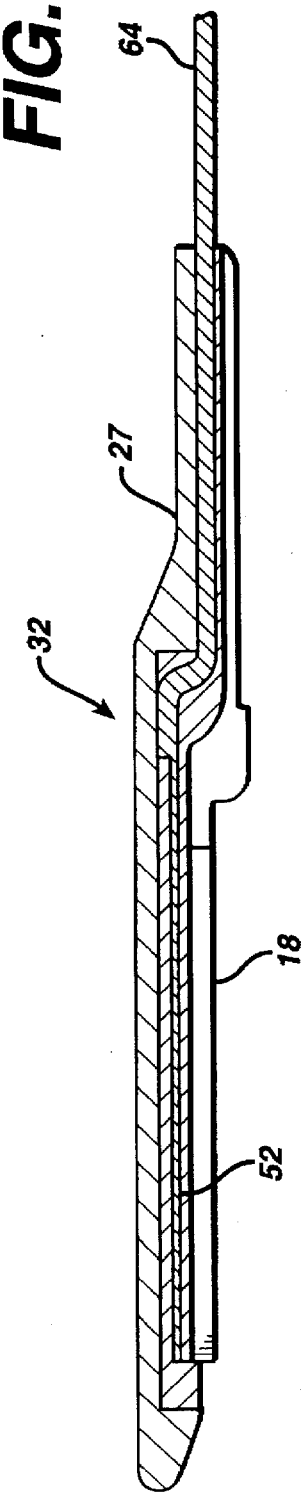

ELECTROSURGICAL HEMOSTATIC DEVICE

This is a continuation-in-part of U.S. application Ser. No. 95,797, filed on Jul. 22, 1993 now U.S. Pat. No. 5,403,372 and U.S. application Ser. No. 96,154, filed on Jul. 22, 1993 (abandoned), both of which are incorporated herein by reference.

FIELD OF THE INVENTION

This invention relates to an electrosurgical instrument for cauterization, coagulation and/or tissue welding in the performance of surgical procedures, especially endoscopic procedures.

BACKGROUND OF THE INVENTION

Surgical procedures requiring cutting of tissue can cause bleeding at the site of the cutting. Various techniques have been adapted to control bleeding with varying degrees of success such as, for example, suturing, applying clips to blood vessels, and stapling, as well as electrocautery and other tissue heating techniques. Advances in tissue joining or welding, tissue repair and wound closure also have permitted surgical procedures previously not possible or too risky.

Surgical staplers have been used for tissue joining, and to provide hemostasis in conjunction with tissue cutting. Such devices include, for example, linear and circular cutting and stapling instruments. Typically, a linear cutter has parallel rows of staples with a slot for a cutting means to travel between the rows of staples. This type of surgical stapler secures tissue for improved cutting, joins layers of tissue, and provides hemostasis by applying parallel rows of staples to layers of surrounding tissue as the cutting means cuts between the parallel rows.

Electrocautery devices have been used for effecting improved hemostasis by heating tissue and blood vessels to cause coagulation or cauterization. Monopolar devices utilize one electrode associated with a cutting or cauterizing instrument and a remote return electrode, usually adhered externally to the patient. More recently, bipolar instruments have been used because the cauterizing current is generally limited to tissue between two electrodes of a tissue treating portion of an instrument.

Bipolar forceps have been used for cutting and/or coagulation in various procedures. Generally, bipolar forceps grasp tissue between two poles and apply electrical current through the grasped tissue. Bipolar forceps, however, have certain drawbacks, some of which include the tendency of the current to arc between poles when tissue is thin or the forceps to short when the poles of the forceps touch. The use of forceps for coagulation is also very technique dependent and the forceps are not adapted to simultaneously cauterize a larger area of tissue. Furthermore, forceps tend to cause areas of thermal spread, i.e., dissipation of heat outside of area defined by grasping or engaging surfaces of the forceps.

SUMMARY OF THE INVENTION

It is therefore an object of the present invention to provide a hemostatic electrosurgical instrument which can efficiently provide hemostasis in multiple tissue types and thicknesses, e.g., in fleshy or vascular tissue areas, and high, low or combination impedance tissues. Hemostasis is used herein to mean generally the arresting of bleeding including by coagulation, cauterization and/or tissue joining or welding.

It is another object of the invention to provide a hemostatic device which is capable of being used to simultaneously cauterize or weld a relatively larger area or length of tissue than in previously known devices.

Another object of the invention is to provide a controlled current delivery path by arranging electrodes to provide a desired current path, preferably through a zone of high tissue compression.

It is another object of the invention to provide a electrocautery device having elongated or bar electrodes.

Another object of the invention to is provide a hemostatic means for providing a line of coagulation adjacent to a cutting path of a cutting means for dividing tissue.

Another object of the invention is to provide a cutting and stapling device with an electrocautery means for tissue welding or cauterization along a cutting path.

These and other objects of the invention are described in an electrosurgical device having an end effector with opposing interfacing surfaces for engaging tissue therebetween, and two electrically opposite electrodes, corresponding to electrically opposite poles, each electrode located on one or both of the opposing surfaces. The electrodes are offset from each other with respect to interfacing surfaces, i.e., they are offset from each other so that they are not diametrically opposed from each other on interfacing surfaces. If the electrodes are on the same surface, they are separated from each other with an insulating material or an insulator (which may include an air gap) which electrically isolates the electrodes.

An electrosurgical instrument of a preferred embodiment compresses tissue in a compression zone between a first interfacing surface and a second interfacing surface and applies electrical energy through the compression zone. The first interfacing surface is comprised of: a first electrode corresponding to a first pole of a bipolar energy source and located on one side lateral to the compression zone; and a second electrode corresponding to a second pole of a bipolar energy source and on the side laterally opposite of the compression zone as the first electrode. The second electrode is located on the same or opposite interfacing surface as the first electrode. This arrangement electrically isolates the two poles and enables the current path between the first and second electrodes to cross through a desired area of compressed tissue.

In a preferred embodiment, the compression zone is an area defined by a compression ridge on one of the interfacing surfaces which compresses the tissue against the other interfacing surface. Also, there may be a compression ridge on both interfacing surfaces. A coagulation zone is defined by the first electrode, the second electrode, and an insulator insulating the first electrode from the second electrode.

It is believed that the tissue compression normalizes tissue impedance by reducing structural differences in tissue which can cause impedance differences. Compression also stops significant blood flow and squeezes out blood and other interstitial fluids which act as a heat sink, particularly when flowing through veins, arteries and other vessels. It is further believed that high compression causes a higher current density to be delivered through compressed tissue in contact with an energy delivering electrode. Thus, it is believed that compression optimizes delivery of energy to tissue in part by preventing excessive thermal dissipation due to blood flow, dissipation through surrounding boundaries, and by enabling quick delivery of a higher current density to a controlled area of tissue. The arrangement of the electrodes, which make up the poles, is important to ensure that the current passing between the two poles passes though the compression zone. Also, the electrode arrangement permits tissue compression without shorting of the instrument poles or electrical arcing common in bipolar instruments.

Thus, the tissue compression and the arrangement of the electrodes permit more efficient cauterization and offer the advantage of achieving hemostasis in a wide range of tissue impedance, thickness and vascularity.

The present invention also provides a device capable of coagulating a line or path of tissue along or lateral to a cut line or a cutting path. In one embodiment, the first electrode and second electrodes each comprise an elongated electrode each on opposite sides and laterally adjacent an insulator forming a ridge to compress the tissue to be cauterized.

In one preferred embodiment, a cutting means for cutting tissue is incorporated into the device and the device provides hemostatic lines adjacent to the path of the cutting means. Of course, cutting may occur at anytime either before, during or after cauterization or welding. In one variation of this preferred embodiment, stapling means is provided on one or both sides of the cutting path.

In one embodiment, an indicator means communicates to the user that the tissue has been cauterized to a desired or predetermined degree.

In one embodiment electrosurgical energy is applied in conjunction with application of one or more tissue fasteners, such as, for example, staples, clips, sutures, absorbable fasteners, etc., with a fastener applier, e.g., a staple driver.

In another embodiment, the coagulation is completed prior to any mechanical cutting, i.e., actuation of the cutting means. If an indicator means is used, once tissue is cauterized, the cutting means may be actuated to cut between the bars while the rows of staples are applied to the tissue.

In another embodiment, the hemostatic device is incorporated into a linear cutter similar to a linear cutting mechanical stapler. In this embodiment the hemostatic device comprises two substantially parallel and joined elongated electrode bars which form the electrically opposite poles, and a slot for a cutting means to travel between the bars. Optionally, one or more rows of staples may be provided on each side of the slot and bars to provide mechanical tissue security or approximation during the healing process. In operation, tissue is clamped between two jaws. Electrical energy in the form of radio frequency current is applied to the compressed tissue to cauterize tissue along the two bars.

A variation of the embodiments described herein may provide a tissue welding or cauterizing and cutting device similar to an intraluminal stapler.

Another embodiment provides a means for detecting abnormal impedances or other electrical parameters which are out of a predetermined range. For example, the means for detecting may be used to indicate when the instrument has been applied to tissue exhibiting impedances out of range for anticipated good coagulation. It may also be used for detecting other instrument abnormalities. It is possible to detect the abnormal condition, for example, by using comparisons of normal ranges of initial tissue impedances in the interface electronics. This could be sensed in the first few milliseconds of the application of RF energy and would not present a significant therapeutic dose of energy, i.e., energy required to cauterize, coagulate or weld tissue. Alternatively a low voltage signal may be applied prior to delivering therapeutic energy to measure tissue impedance. A warning mechanism may be used to warn the user when the impedance is out of range. Upon repositioning of the instrument, the same measurement criteria would apply and if the tissue impedance was again out of range, the user would again be warned. This process would continue until the normal impedance range was satisfied and good coagulation could be anticipated.

These and other objects of the invention will be better understood from the following attached Detailed Description of the Drawings, when taken in conjunction with the Detailed Description of the invention.

DETAILED DESCRIPTION OF THE DRAWINGS

FIG. 7 is a bottom isolated view of the anvil jaw of the instrument of FIG. 1;

FIG. 8 is a top isolated view of a cartridge of the instrument of FIG. 1;

FIG. 9 is a side cross sectional view of the jaw of FIG. 7 along the line 9—9;

DETAILED DESCRIPTION OF THE PREFERRED EMBODIMENTS

Figure 1:
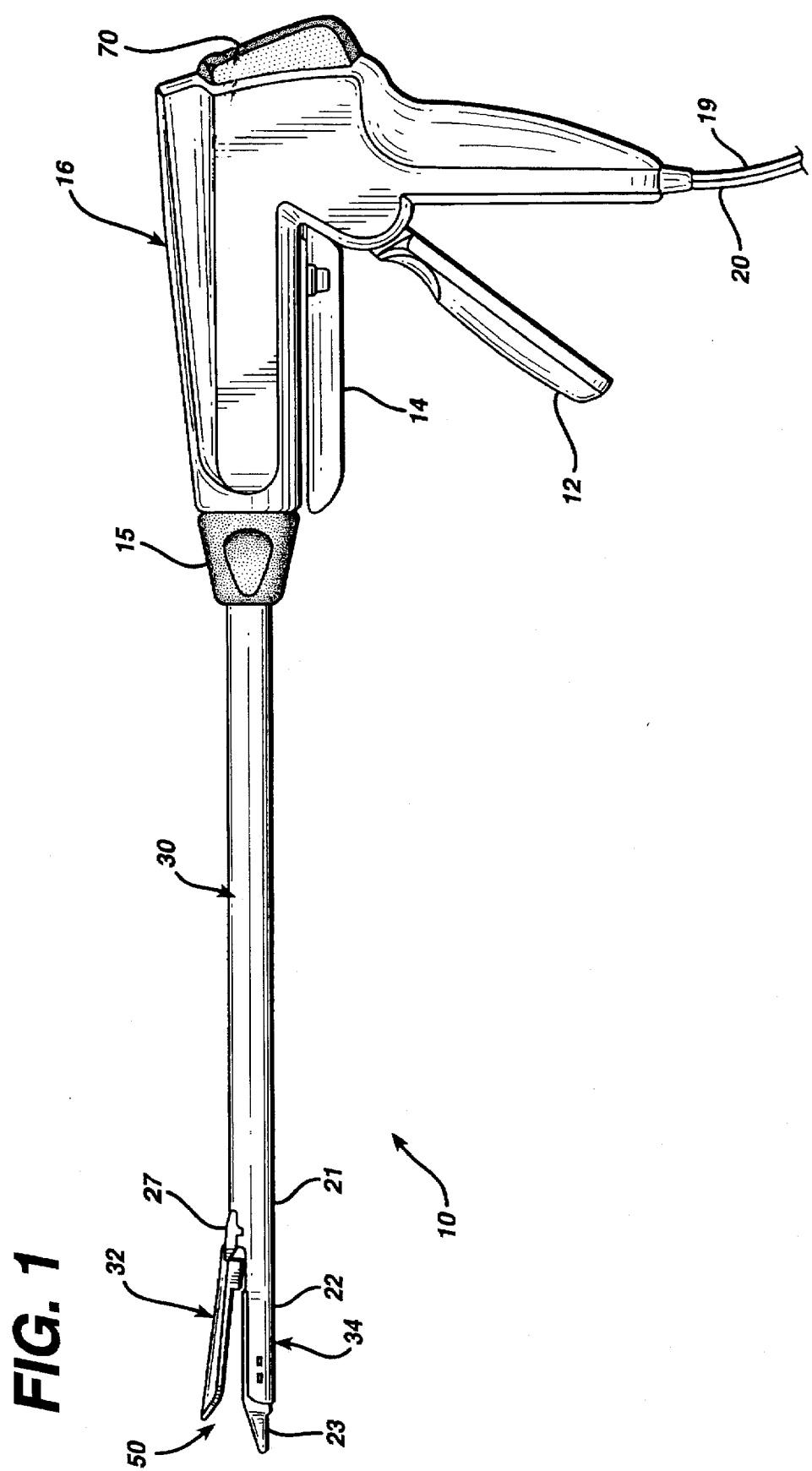
FIG. 1 is a side elevational view of an endoscopic electrocautery linear stapling and cutting instrument of one embodiment of the present invention.
Figure 2:
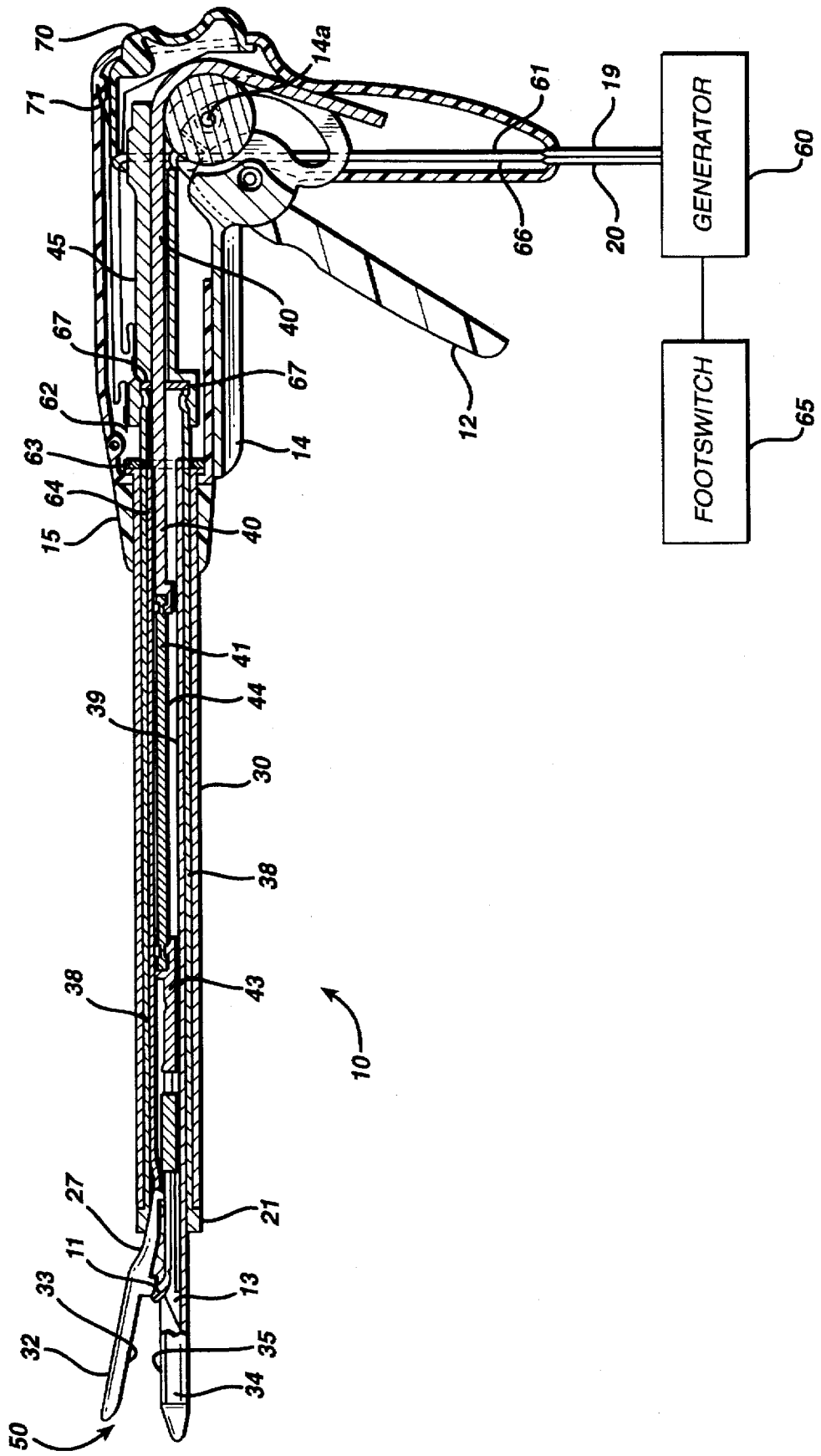
FIG. 2 is a side cross sectional view of the instrument of FIG. 1.
Figure 3:
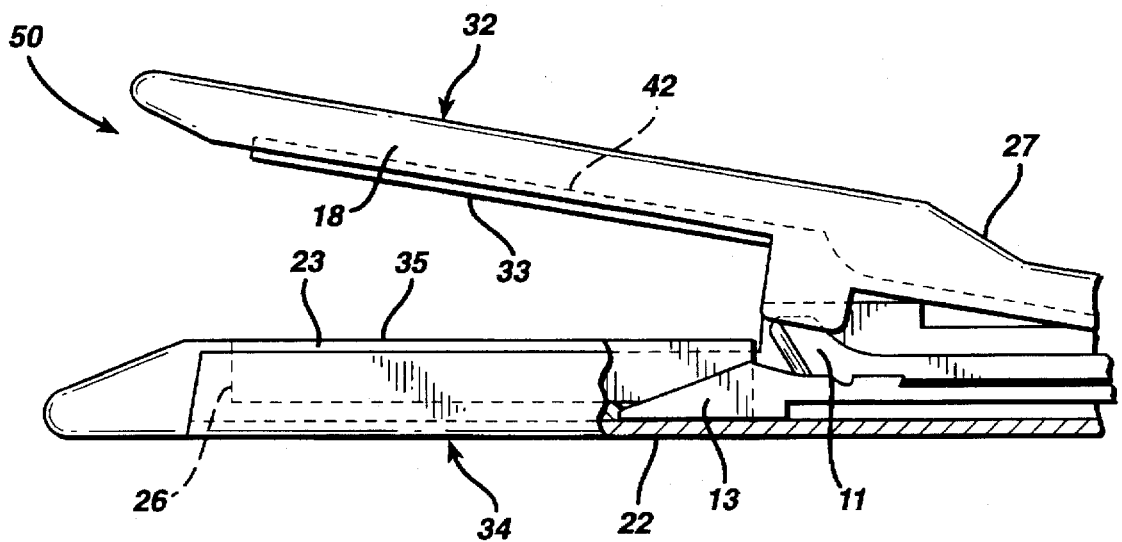
FIG. 3 is a partial cross sectional view of the distal end of the instrument of FIG. 1 in an open position.
Figure 4:
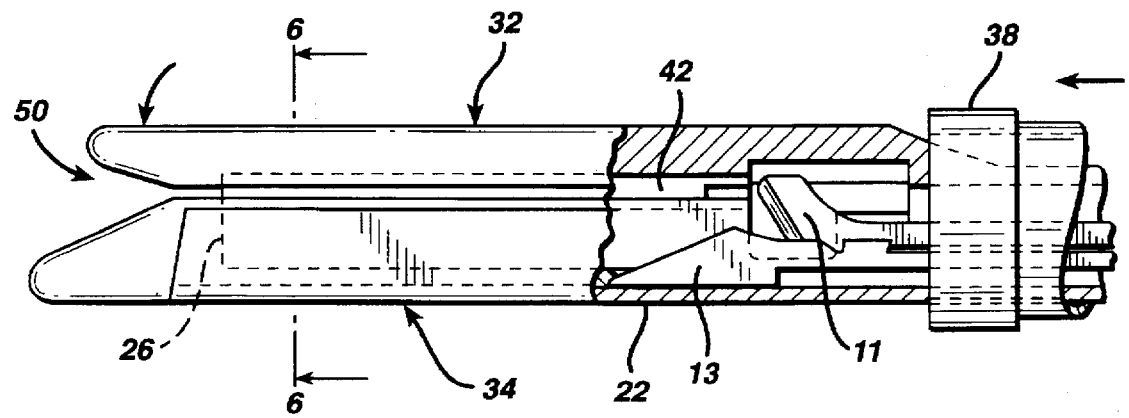
FIG. 4 is a partial cross sectional view of the distal end of the instrument of FIG. 1 in a closed, unfired position.
Figure 5:
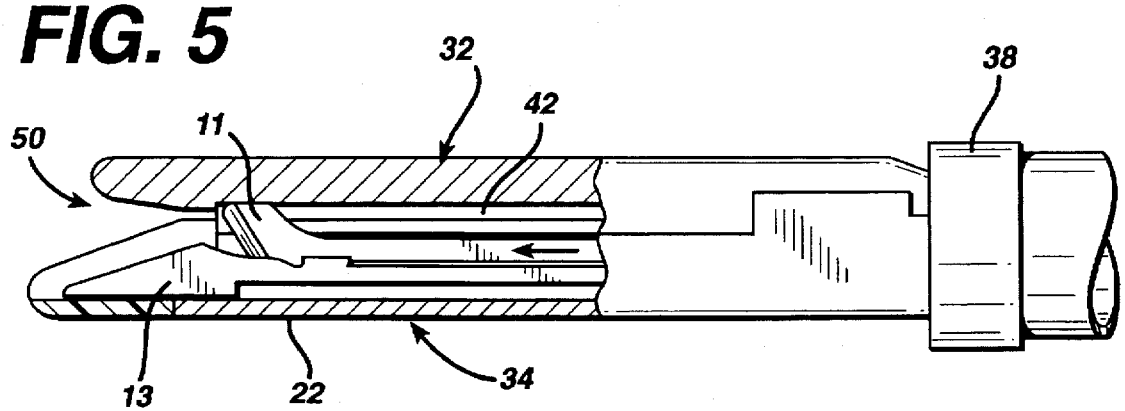
FIG. 5 is a partial cross sectional view of the distal end of the instrument of FIG. 1 in a closed, fired position.

Referring now to FIGS. 1–9, there is illustrated a preferred embodiment of the present invention. An endoscopic electrocautery linear cutting and stapling instrument 10 is shown having a body 16 coupled to a shaft 30 with a lumen extending therethrough and an end effector 50 extending from the distal end 21 of the shaft 30. The shaft 30 is formed of an insulative material and has an electrically conductive sheath 38 extending through its lumen. A channel 39 extending through the sheath 38 guides co-axial movement of a driver means 44 within the channel 39. In this particular embodiment, the driver means 44 includes a firing trigger 14 associated with the body 16, coupled to a flexible firing rod 40 coupled to a driving rod 41, coupled to a block 43. The block 43 is coupled to a cutting means 11 and a staple driving wedge 13, which the driving means 44 advances by way of the block 43 into the end effector 50.

The end effector 50 comprises two interfacing jaw members 32, 34. The end effector 50 is secured by way of jaw member 34 to the channel 39. The jaw member 32 is movably secured to jaw member 34. The body 16 has a clamping trigger 12 for closing the jaws 32, 34 which longitudinally advances a close rack 45 coupled to the proximal end of the sheath 38. The close rack 45 advances the sheath 38 co-axially through the shaft 30. The sheath 38 advances over a camming surface 27 of jaw 32 to close the jaws 32 and 34 onto tissue situated between the jaws. As described in more detail below, the close rack 45 also acts as a switch to close the circuit which communicates electrical energy to the end effector 50.

Referring now to FIGS. 3–9 an enlargement of the end effector 50 of the instrument 10 is illustrated. The jaw members 32 and 34 are shown in an unclamped position in FIG. 3, in a clamped, unfired position in FIG. 4 and in a clamped, fired position in FIG. 5. A knife channel 26 defines a plane bisecting the first and second interfacing surfaces 33, 35. Jaw member 32 comprises an anvil 18. The anvil 18 includes a first electrode 52 extending longitudinally with respect to the jaw 32, on a first lateral side 81 of the anvil 18 with respect to the plane, and a second electrode 80 extending longitudinally with respect to jaws 32 on the opposite lateral side 82 of the anvil 18 with respect to the plane. The first electrode 52 and second electrode 80 are electrically isolated from each other by an insulator 55 extending through the middle of the anvil 18.

Figure 6:
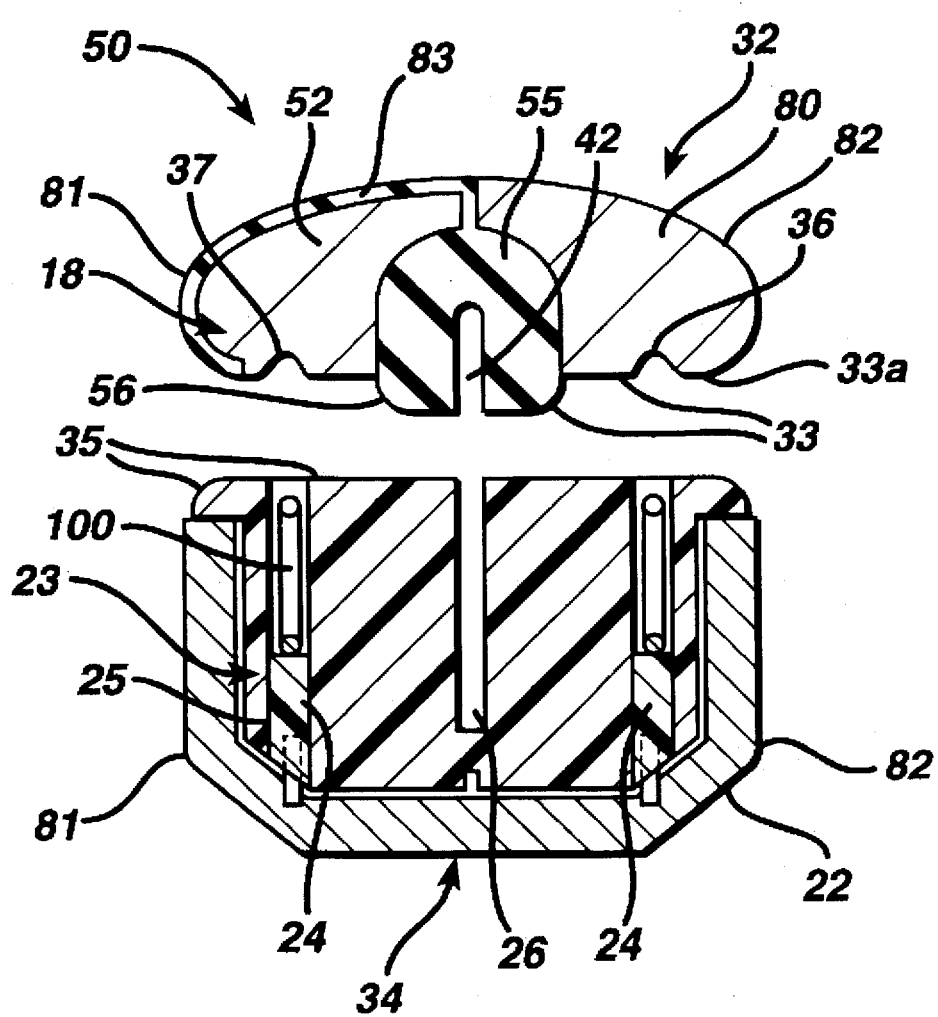
FIG. 6 is a front cross sectional view of the distal end of the instrument of FIG. 3 taken along the line 6—6.

Jaw member 32 has an inner surface 33 which faces an inner surface 35 of jaw 34. The first and second electrodes 52, 80 extend proximally to distally along interfacing surface and are separated by insulator 55 forming a compression ridge 56, proximally to distally, in the interfacing surface 33. The ridge 56 extends out relative to anvil portion 33a of the inner surface 33 (FIG. 6). The insulator 55 includes a knife channel 42 extending longitudinally through the insulator 55 to generally form a U-shape and permit passage of a cutting element through slot 42. Two series of pockets 36, 37 located on anvil 18, for receiving staple ends, extend along the inner surface 33, on each side 81, 82 lateral to and outside of insulator 55. The electrodes 52, 80 are formed of an electrically conductive material such as aluminum and act as first and second electrically opposite poles.

Jaw member 34 comprises a cartridge channel 22 and a cartridge 23. The cartridge 23 includes a track 25 for the wedge 13, knife channel 26 extending longitudinally through the center of the cartridge 23, a series of drivers 24 extending into track 25 and staples 100 arranged in two single rows. When tissue is engaged between the jaws 32, 34, the driver means 44 may be actuated or fired using trigger 14 to advance the cutting means 11 and wedge 13 through the engaged tissue to staple and cut the tissue. When the firing mechanism 14 is actuated, the wedge 13 is advanced through the track 25 causing the drivers 24 to displace towards the staples 100, thereby driving the staples 100 through tissue and into anvil pockets 36, 37.

A knob 15 located on the distal end of the body 16 rotates the shaft 30, sheath 38, channel 39 and end effector 50 which are directly or indirectly coupled to the knob 15 so that the knob 15 may be used for rotational placement of the end effector jaws 32,34.

Bipolar energy is supplied to the end effector 50 from an electrosurgical generator 60 through wires 19, 20 extending into the body 16 of the instrument. The generator 60 is user controlled by way of a footswitch 65.

Wire 19 which provides electrical current to the first pole, is coupled through a wire or other electrical contact means 61 to electrical contact 62, associated with the first pole, located on the distal end of close rack 45. Wire 20 which carries the current of the opposite pole, is coupled through a wire or other electrical contact means 66 to a disc contact 67 located at the distal end of the close rack 45 and electrically isolated from contact 62.

A disc contact 63, associated with the first pole, located at the distal end of the body 16 is in electrical communication with a wire or other contact means 64. Contact means 64 extends through channel 39 to end effector jaw 32 where it contacts the first electrode 52. The disc contact 63 permits the knob 15 to rotate while contact is maintained between the disc contact 63 and the contact means 64. The contact means 64 is electrically insulated from the sheath 38.

When the clamping trigger 12 is actuated, the close rack 45 moves distally so that the contact 62 comes in electrical communication with the disc contact 63, and the disc contact 67, associated with the second electrode 80, comes in electrical contact with the electrically conductive sheath 38. The sheath 38 moves over the camming surface 27 of the electrically conductive second lateral portion 82 of the anvil 18. The first lateral portion 81 of the anvil 18 is coated with an insulative material 83 except where the electrode 52 is exposed at interfacing surface 33. Thus, the sheath 38 does not come into electrical contact with the first electrode 52. The electrical circuit is closed when and only when the clamping trigger 12 is closed.

In operation, the end effector 50 of the instrument is located at a tissue site where tissue is to be cut. The jaw members 32, 34 are opened by pressing a release button 70 which releases a button spring 71 and permits the close rack 45 to move proximally. Tissue is then placed between the interfacing inner surfaces 33, 35 respectively of the jaw members 32, 34. The clamping trigger 12 is squeezed to cause the sheath 38 to move over the camming surface 27 and thereby close the jaws 32, 34 and simultaneously close the electrical circuit as described above. The insulator 55 which forms the ridge 56, compresses the tissue against the inner surface 35 of jaw member 34. A user then applies RF energy from the generator 60 using the footswitch 65 or other switch. Current flows through the compressed tissue and between the first electrode 52 and the second electrode 80.

Preferably the bipolar energy source is a low impedance source providing radio frequency energy from about 300 kHz to 3 MHZ. Preferably, the current delivered to the tissue is from 0.1 to 1.5 amps and the voltage is from 30 to 200 volts RMS.

An audible, visible, tactile, or other feedback system may be used to indicate when sufficient cauterization has occurred at which point the RF energy may be turned off. An example of such a feedback system is described below. After the RF energy is turned off, the cutting means 11 is advanced and the staples 100 are fired using the firing trigger 14. Firing is accomplished by rotating the firing trigger 14 acting as a lever arm about pivot 14a. The driver means 44 advances the cutting means 11 and wedge 13. The cutting means 11 cuts the tissue in between the electrodes 52, 80 where the tissue has been cauterized. Thus, the cut line is lateral to the coagulation lines formed by the electrodes 52, 80. The wedge 13 simultaneously advances the drivers 24 into the staples 100 causing the staples 100 to fire through tissue and into the pockets 36, 37 of the anvil 18. Staples 100 are applied in a longitudinal single row on each side of the cutting means 11 as the cutting means cuts the tissue.

Operation of linear staplers are known in the art and are discussed, for example, in U.S. Pat. Nos. 4,608,981, 4,633, 874, and U.S. application Ser. No. 07/917,636 incorporated herein by reference.

The above described preferred embodiment may be incorporated into a circular stapler. Operation of circular staplers is known in the art and is described, for example in U.S. Pat. No. 5,104,025 incorporated herein by reference. A variation of the embodiments described herein may provide a tissue welding and cauterizing cutting device similar to an intraluminal stapler. In this embodiment, a device similar to that described in Parent application Ser. No. 08/095,797 filed on Jul. 22, 1993 is provided. The electrodes are formed in two concentric circle electrodes separated by an insulator. The electrodes are located radially inward or radially outward of the insulator which forms the compression ridge and on either of the interfacing surfaces. The electrodes of the stapling embodiment of the circular cutting device may be located on either the stapler cartridge or the anvil.

In a embodiment, the cartridge provides multifire stapling capabilities by having single rows of staples, as opposed to the convention double row of staples of the cartridges in the laparoscopic stapling and cutting devices presently in use. In order to provide better hemostasis, this type of stapler was designed to provide a double row of staples for each parallel row. Because of the size of the space necessary to contain the double row of staples, a refireable cartridge with stacked staples has not been preferred because of the additional space required for stacking staples. In the multifire stapling embodiment a single row of staples is used. Using a single row of staples permits stacking of staples in the space previously occupied by the second row of staples, providing multifire capabilities. The device of the present may however, if desired, include double, triple, etc., staple rows. Also, in a further embodiment, no staples are required and the electrical coagulation lines provide the necessary hemostasis or tissue welding effect.

A preferred embodiment of the present invention includes a feedback system designed to indicate when a desired or predetermined degree of coagulation has occurred. This is particularly useful where the coagulation zone is not visible to the user. In a particular embodiment, the feedback system measures electrical parameters of the system which include coagulation level.

The feedback system may also determine tissue characteristics at or near a coagulation zone which indicate degree of coagulation. The electrical impedance of the tissue to which the electrical energy is applied may also be used to indicate coagulation. Generally, as energy is applied to the tissue, the impedance will initially decrease and then rise as coagulation occurs. An example of the relationship between electrical tissue impedance over time and coagulation is described in Vaellfors, Bertil and Bergdahl, Bjoern "Automatically controlled Bipolar Electrocoagulation," Neurosurg. Rev. p. 187–190 (1984) incorporated herein by reference. Also as desiccation occurs, impedance increases. Tissue carbonization and or sticking to instrument as a result of over application of high voltage may be prevented using a feedback system based on tissue impedance characteristics. Other examples of tissue characteristics which may indicate coagulation include temperature and light reflectance.

Figure 10:
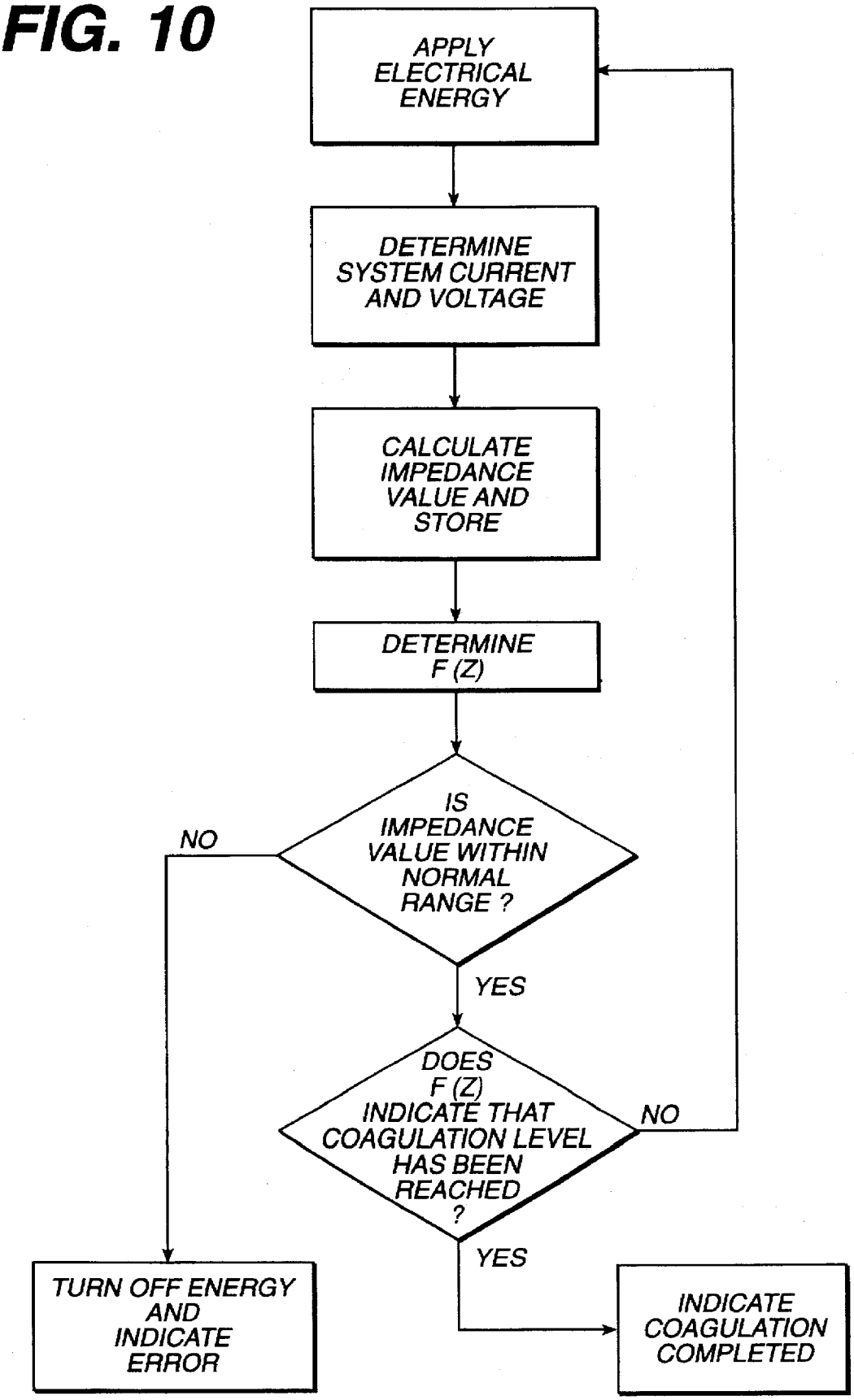
FIG. 10 is a flow chart illustrating a feedback system of the present invention.

Referring to FIG. 10, a flow chart illustrates a feedback system which is implemented in a preferred embodiment of the present invention. First, energy is applied to the tissue. Then the system current and voltage applied to the tissue is determined. The impedance value is calculated and stored. Based on a function of the impedance, for example, which may include the impedance, the change in impedance, and/or the rate of change in impedance, it is determined whether desired coagulation has occurred. If coagulation has occurred to a predetermined or desired degree, an indication means indicates that the energy should be turned off. Such an indication means may include a visible light, an audible sound or a tactile indicator. The feedback means may also control the generator and turn the energy off at a certain impedance level. An alternative embodiment provides a continuous audible sound in which the tone varies depending on the impedance level. An additional feature provides an error indication means for indicating an error or instrument malfunction when the impedance is below a normal minimum and/or above a maximum range.

Figure 11:
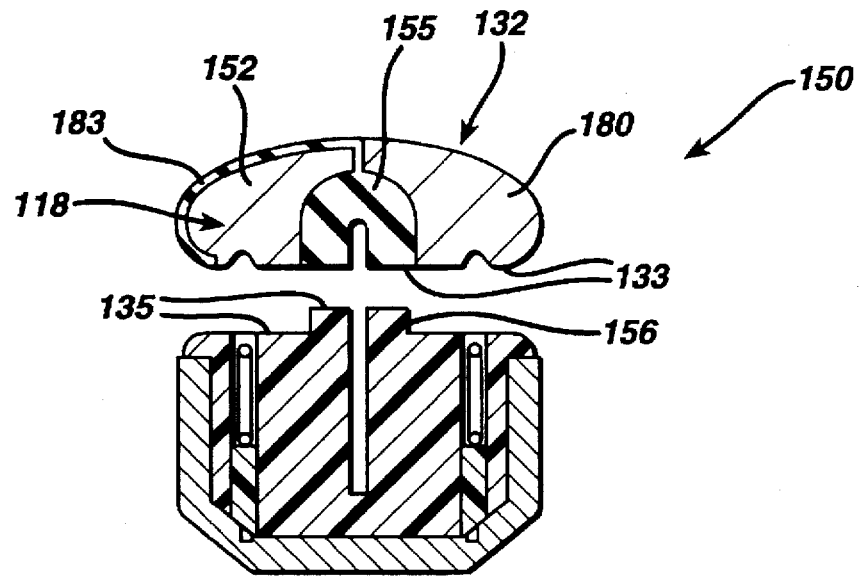
FIG. 11 illustrates a front cross-sectional view of the end effector having an alternative electrode configuration.

Referring now to FIG. 11, there is illustrated an alternative embodiment of an end effector 150 of the present invention. A jaw member 132 is illustrated having an anvil 118 including a first interfacing surface 133 comprised of a first electrode 152 of a first electrical potential and a second electrode 180 of an opposite electrical potential. The first and second electrodes 152, 180 extend proximally to distally along interfacing surface 133 and are separated by insulator 155. A second opposing interfacing surface 135 includes a compression ridge 156 formed therein and extending proximally to distally along the interfacing surface 135. The compression ridge 156 is arranged to compress tissue against the insulated portion of the first interfacing surface and is electrically isolated from the first and second electrodes. First and second electrodes 152, 180 are adapted to be in electrical contact with an energy source in the same manner as first and second electrodes 52, 80 respectively of FIG. 6. Insulation 183 prevents electrical contact of electrode 152 with sheath 38.

Figure 12:
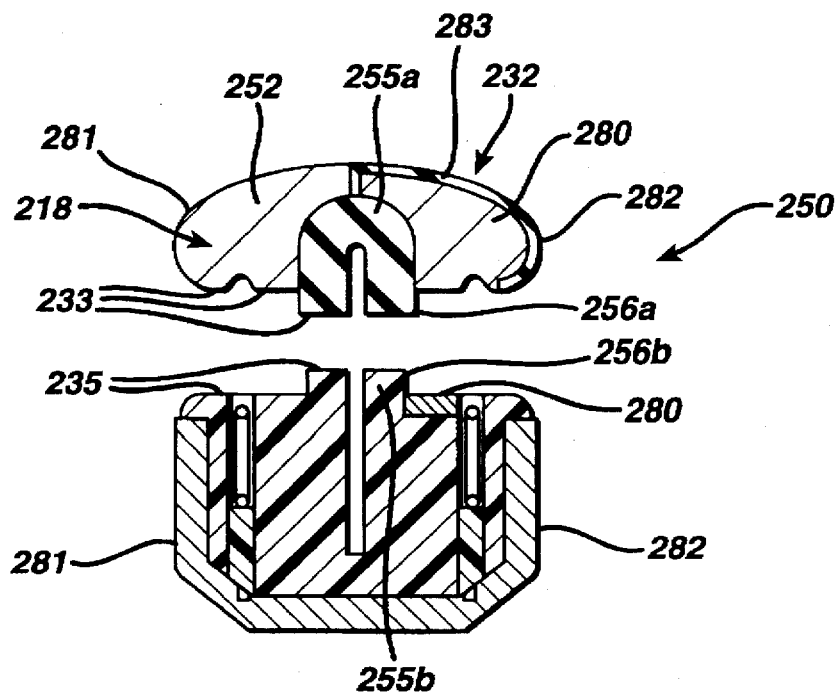
FIG. 12 illustrates a front cross-sectional view of the end effector having an alternative electrode configuration.

Referring now to FIG. 12, there is illustrated another alternative embodiment of the present invention. End effector 250 includes jaw member 232 having an anvil 218 including a first interfacing surface 233. The anvil 218 is comprised of a first electrode 252 of a first electrically potential on a first lateral side 281 of the end effector 250. The first electrode 252 extends proximally to distally along interfacing surface 233. An insulator 255a forms a ridge 256a extending proximally to distally along interfacing surface 233 and separates the first electrode 252 from the opposite or second lateral side 282 of the end effector 250. The end effector 250 includes a second interfacing surface 235 opposite the first interfacing surface 233. Second interfacing surface 235 includes a second electrode 280 located on second lateral side 282 of end effector 250. A second insulator 255b forms a ridge 256b in interfacing surface 235 extending proximally to distally with respect to the end effector 250. Ridge 256a and 256b oppose each other. In this embodiment electrical energy is supplied to the first and second electrodes in a manner similar to the embodiment in FIG. 6 except that the first electrode 252 is in electrical contact with a sheath 38 and electrode 280 is in contact with contact means 64. Insulation 283 prevent electrical contact of the second lateral side 282 of first jaw 232 with sheath 38 and thereby prevents shorting or arcing with electrode 280.

Figure 13:
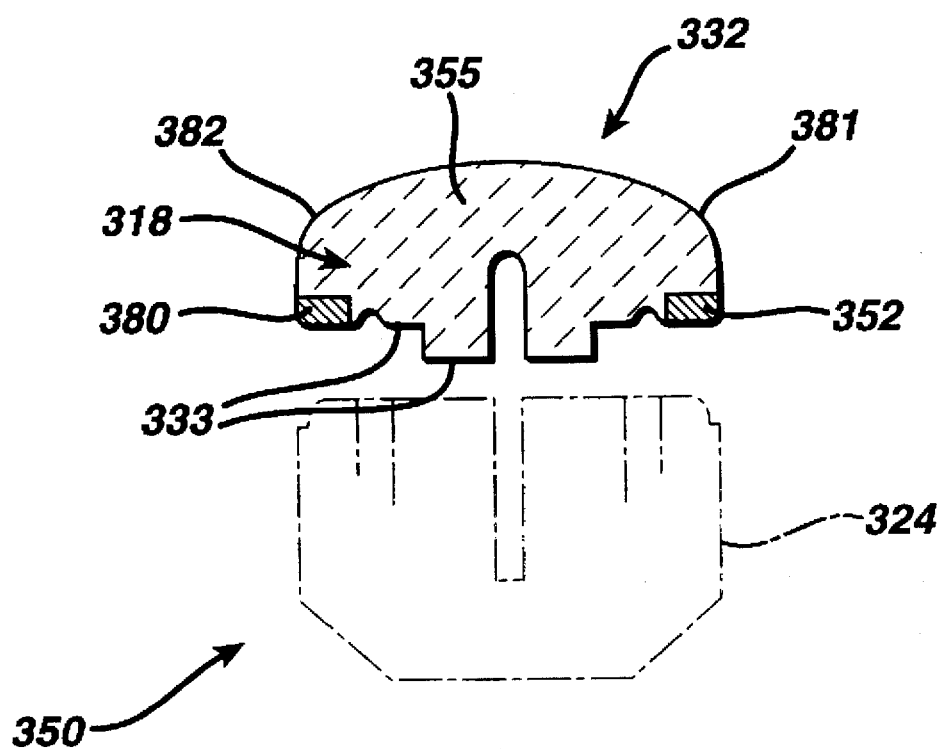
FIG. 13 illustrates a front cross-sectional view of the end effector having an alternative electrode configuration.

Referring now to FIG. 13, there is illustrated another embodiment of the present invention. End effector 350 includes jaw member 332 having an anvil 318 formed of an electrically insulative material such as a ceramic insulator. The anvil 318 includes a first electrode 352 of a first electrical potential on a first lateral side 381 of the end effector 350. The first electrode 352 is disposed on anvil 318 and extends proximally to distally along interfacing surface 333. A second electrode 380 is disposed on the anvil 318 on a second lateral side 382 on the opposite lateral side from the first lateral side 381. The second electrode 380 extends proximally to distally along interfacing surface 382. Insulator 355 forms a ridge on interfacing surface 333 located between the first electrode 352 on the first side 381 and the second electrode 380 on the lateral side 382 of the end effector.

Alternative electrical connections may be used to provide or deliver electrical current from an electrosurgical generator and through the handle 16 of the device to the electrodes at the end effector 50, 150, 250 or 350. For example, wireforms, contact blocks, and low impedance snap fit contacts may be used. The device may also provide a lockout which prevents firing of RF energy until the clamping trigger 12 has been closed, and which prevents cutting element actuation and stapling until the clamping trigger 12 is closed and RF energy has been applied. An example of these features are described in co-pending U.S. application entitled "Impedance Feedback Monitor with Query Electrode for Electrosurgical Instrument" to David Yates et al., filed on Dec. 22, 1994, incorporated herein by reference.

Alternative variations of the described invention may include, for example, compression ridges formed in either one or both interfacing surfaces, electrodes located on the first, second or both interfacing surface; electrodes or multiple electrodes associated with each pole located on one or both of the interfacing surfaces. Also the device may have no compression ridges.

Several variations of this invention have been described in connection with specific embodiments involving endoscopic cutting and stapling. Naturally, the invention may be used in numerous applications where hemostasis in desired including instruments without cutting or stapling. Accordingly, will be understood by those skilled in the art that various changes and modifications may be made in the invention without departing from its scope, which is defined by the following claims and their equivalents.

What is claimed is:

1. An electrosurgical device having an end effector capable of receiving bipolar energy therein, said end effector comprising:
    first and second opposing interfacing surfaces, said interfacing surfaces capable of engaging tissue therebetween;
    electrically isolated first and second poles comprised of electrically opposite first and second electrodes respectively said electrodes capable of conducting bipolar energy therethrough;
    said first and second electrodes located on said first surface and separated by an insulator;
    said electrodes arranged so that bipolar energy may be communicated between said poles through the tissue engaged by said interfacing surfaces; and
    wherein said insulator forms a compression ridge for compressing tissue between said interfacing surfaces.

2. The electrosurgical device of claim 1 wherein said first and second electrodes are arranged to provide a current path through tissue compressed by said compression ridge.

3. The electrosurgical device of claim 1 wherein said second interfacing surface comprises a compression ridge formed of an insulator.

4. The electrosurgical device of claim 1 wherein said device includes a cutting element arranged on said device to divide tissue engaged by said end effector, through a cutting line, when said cutting element is actuated.

5. The electrosurgical device of claim 4 wherein said insulator includes a slot arranged to receive said cutting element and to permit said cutting element to move through said cutting line.

6. The electrosurgical device of claim 4 wherein said end effector comprises at least one tissue fastener and an applier located with said end effector, said applier adapted to apply the fastener to tissue engaged by the end effector.

7. The electrosurgical device of claim 4 wherein said end effector comprises at least one staple and at least one driver adapted to apply said at least one staple lateral to said cutting line.

8. The electrosurgical device of claim 1 wherein said end effector further comprises:
    at least one tissue fastener and at least one applier adapted to apply said at least one tissue fastener to tissue engaged by said end effector.

9. An electrosurgical device having an end effector capable of receiving bipolar energy therein, said end effector comprising:
    first and second opposing interfacing surfaces, said interfacing surfaces capable of engaging tissue therebetween;
    electrically isolate first and second poles comprised of respectively electrically opposite first and second electrodes capable of conducting bipolar energy therethrough;
    said first and second electrodes located on said first surface and separated by an insulator;
    said electrodes arranged so that bipolar energy may be communicated between said poles through the tissue engaged by said interfacing surfaces; and
    wherein said second interfacing surface comprises a compression ridge formed of an insulating material.

10. The electrosurgical device of claim 9 wherein said device includes a cutting element arranged on said device to divide tissue engaged by said end effector, through a cutting line, when said cutting element is actuated.

11. The electrosurgical device of claim 10 wherein said insulator includes a slot arranged to receive said cutting element and to permit said cutting element to move through said cutting line.

12. The electrosurgical device of claim 10, wherein said end effector comprises at least one fastener and at least one applier adapted to apply said at least one fastener lateral to said cutting line.

13. The electrosurgical device of claim 10 wherein said end effector comprises at least one staple and at least one driver adapted to apply said at least one staple lateral to said cutting line.

14. The electrosurgical device of claim 9 wherein said end effector further comprises:
    at least one tissue fastener and at least one applier adapted to apply said at least one tissue fastener to tissue engaged by said end effector.

15. An electrosurgical device having an end effector capable of receiving bipolar energy therein, said end effector comprising:
    first and second opposing interfacing surfaces, said interfacing surfaces capable of engaging tissue therebetween;
    a longitudinal plane bisecting said first and second surfaces;
    first and second sides laterally opposite of each other with respect to the longitudinal plane;
    an insulator located between said first and second sides wherein said insulator forms a compression ridge in either the first or second interfacing surface;
    electrically isolated first and second poles comprised of electrically opposite first and second electrodes respectively, said electrodes capable of conducting bipolar energy therethrough;
    each of said first and second electrodes located on at least one of said first and second interfacing surfaces; and said first electrode located on said first side and the second electrode located on said second side.

16. The electrosurgical device of claim 15 wherein said first electrode is located on said first interfacing surface and wherein said second electrode is located on said second interfacing surface.

17. The electrosurgical device of claim 15 wherein a said insulator forms a compression ridge in said first interfacing surface and wherein a said insulator forms a compression ridge in said second interfacing surface.

* * * * *